United States Patent

Shober, Jr. et al.

[11] Patent Number: 5,265,822
[45] Date of Patent: Nov. 30, 1993

[54] IV TUBE SUPPORT ASSEMBLY

[76] Inventors: Robert C. Shober, Jr., P.O. Box 143, Alvaton, Ky. 42122; Robert L. Watson, 1600 Singletree Way, Bowling Green, Ky. 42103

[21] Appl. No.: 912,761

[22] Filed: Jul. 13, 1992

[51] Int. Cl.5 .............................................. B65H 75/38
[52] U.S. Cl. .................................. 242/86.1; 604/261
[58] Field of Search ................ 242/85, 85.1, 86, 86.1, 242/96, 100, 100.1, 115, 117, 118, 118.4, 118.41, 125, 125.1, 125.2; 604/259, 261

[56] References Cited

U.S. PATENT DOCUMENTS

| | | | |
|---|---|---|---|
| 1,408,261 | 2/1922 | Brookhart. | |
| 1,498,055 | 6/1924 | Martin et al. | 604/261 |
| 2,683,937 | 7/1952 | Criswell | 33/217 |
| 2,923,297 | 2/1960 | Holt | 604/261 |
| 3,095,159 | 6/1963 | Stacy et al. | 242/96 |
| 3,443,771 | 9/1967 | Doty | 242/85.1 |
| 3,743,209 | 7/1973 | Anderson | 242/118.61 |
| 3,758,045 | 9/1973 | Allen | 242/125.2 |
| 4,195,794 | 4/1980 | Ricci et al. | 242/96 X |
| 4,258,843 | 3/1981 | Wymer | 206/63.3 |
| 4,387,863 | 7/1983 | Edmonston et al. | 242/118.4 |
| 4,534,522 | 8/1985 | Spence | 242/172 |
| 4,616,790 | 10/1986 | Beltran | 242/85.1 |
| 4,667,896 | 5/1987 | Frey et al. | 242/118.41 |
| 4,721,268 | 1/1988 | Lerner et al. | 242/85.1 |
| 4,739,945 | 4/1988 | Yokoe | 242/118.41 |
| 4,802,638 | 2/1989 | Burger et al. | 242/85.1 |
| 4,903,826 | 2/1990 | Pearce | 242/96 X |
| 4,913,369 | 4/1990 | Lia et al. | 242/96 |
| 5,071,082 | 12/1991 | Lefevre et al. | 242/115 X |

FOREIGN PATENT DOCUMENTS

| | | | |
|---|---|---|---|
| 62-109627 | 5/1987 | Japan | 242/117 |
| 2035957 | 6/1980 | United Kingdom | 242/118.4 |

Primary Examiner—Daniel P. Stodola
Assistant Examiner—John P. Darling
Attorney, Agent, or Firm—Walter C. Farley; K. L. Orzechowski

[57] ABSTRACT

An assembly for supporting and storing an intravenous supply tube and coupling device having a septum includes an elliptical body capable of having the tubing wound thereon and first and second flanges extending radially outwardly from the body. Each flange includes one or more slots for removably receiving the tubing and securing the tubing in place. The assembly is able to hold the tubing and coupling in place while a hypodermic needle is inserted into the coupling to shield the operator's hand to thereby reduce the risk of injury to the operator. In further embodiments two or more assemblies are coupled together in a ganged fashion.

20 Claims, 3 Drawing Sheets

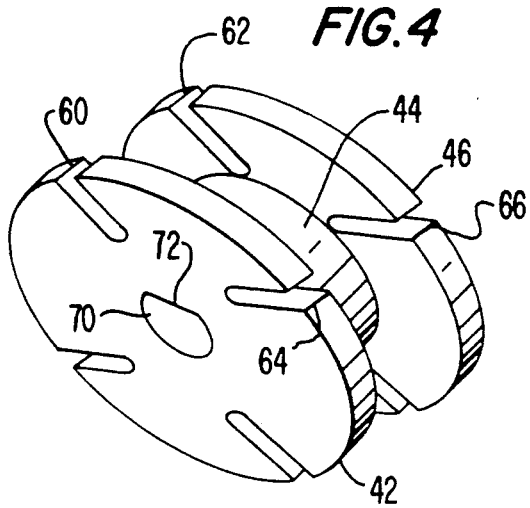
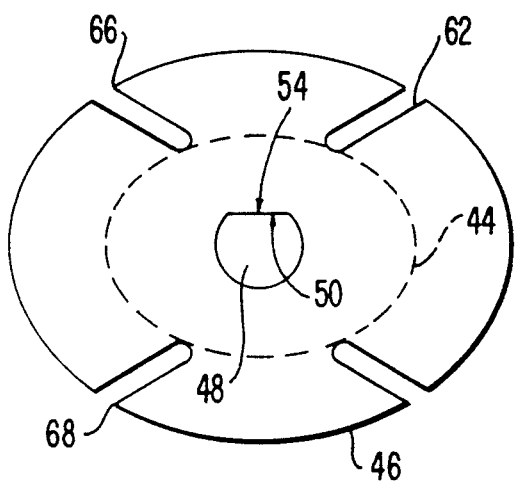
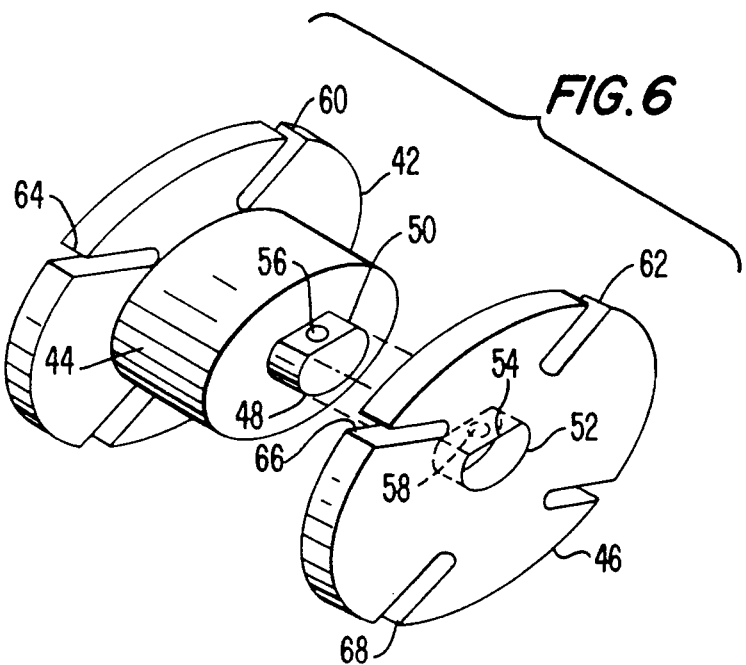

5,265,822

IV TUBE SUPPORT ASSEMBLY

FIELD OF THE INVENTION

The present invention is directed to a device for supporting and stabilizing an intravenous (IV) tube without restricting the flow of fluids. More particularly, the invention relates to a device for temporarily storing excess length of an IV tube, for supporting the tube and for stabilzing an injection port to facilitate use of the port and to reduce the risk of injury while introducing a substance into the tube.

BACKGROUND OF THE INVENTION

In the medical field it is common practice to supply blood and other fluids to the patient intravenously. Standard intravenous (IV) supply devices include an intravenous catheter penetrating the skin and coupled to a supply tube. The supply tube is typically connected to a supply bag or pouch from which the contents are introduced to the patient by gravity. Alternatively, the supply tube may be connected to a standard infusion pump to provide a more accurate and controlled rate of flow through the IV tube.

The standard supply tube is formed from a pliable, clear plastic material which is easily twisted and handled. However, the flexible nature of the tubing can result in the tubing becoming tangled during use. The supply tubing is often used in lengths of four or more feet, depending on the patient, which can further result in the excess length of tubing becoming tangled. The tangling of the supply tubing can result in the tubing being pinched or otherwise constricted to reduce the supply of fluid to the patient. The tangling and/or snagging of the tubing may not be observed for some time and can result in injury to the patient.

There is therefore a need for a device which is able to reduce the risks of tangling an intravenous supply tube without interfering with the flow of fluids. There is further a need for a device which is able to store excess lengths of supply tubing during use and to permit safer use of the injection ports.

In recent years attention in the medical field has been directed to the prevention of the transmission of infectious diseases through normal contact with patients. Only recently has the medical profession become acutely concerned with transmission of infectious diseases from the patient to the health care personnel, and vice versa, during routine treatment. In particular, the medical profession is now actively considering new techniques and devices to prevent the accidental transmission of the HIV virus (AIDS), hepatitis and other blood-borne diseases between the health care personnel and patients.

In several instances, doctors and nurses have contracted hepatitis or the AIDS virus by accidentally puncturing a finger, hand or other body part with a hypodermic needle which has been in contact with a patient infected with hepatitis or the AIDS virus. One of the more common manners in which health care personnel are at risk and have become infected is during injection with a hypodermic needle when the needle slips or breaks and is accidentally plunged into the hand of the person administering the care. Accidents have occurred during injection directly into the patient and also during injection into the coupling of an IV tube.

It is common practice to administer drugs to a patient by inserting a syringe with a needle into a y-shaped coupling in the IV supply tube. This operation typically requires forcing the hypodermic needle with one hand through a puncturable septum in the coupling while the coupling is held with the other hand. The coupling is usually quite small and difficult to handle, thereby creating a high risk of injuring the operator while attempting to insert the needle. There is, therefore, a need for a device capable of supporting an IV supply tube and stabilizing the Y-coupling injection port safely to reduce the risk of injury to the operator while attempting to introduce a drug or other material to the IV tube by inserting a hypodermic needle into the IV tube.

The prior art includes devices capable of storing lengths of tubing and the like, but those devices do not deal adequately with problems specific to tubing through which fluid must flow slowly and reliably, nor do they assist in the solution of the safety problems discussed above.

SUMMARY OF THE INVENTION

The present invention is directed to an apparatus for supporting an intravenous tube during use to prevent tangling with the patient or equipment. A particularly advantageous feature of the invention is the capability of supporting the IV tube and stabilizing a puncturable coupling in a manner to significantly reduce the risk of injury to the healthy care professional and the patient without restricting flow of fluids through the tube. The apparatus effectively supports the IV tube and the coupling such that the health care professional is able to easily insert a hypodermic needle through a coupling to deliver medication to a patient without risk of the needle puncturing a hand or finger of the operator.

The apparatus of the assembly has the further advantage of providing a storage means for the excess length of tubing without interfering with the flow of fluid at the coupling member and the insertion of a hypodermic needle into the coupling. The apparatus is further able to provide storage of the supply tubing without restricting the flow of the fluids through the tubing.

The apparatus is simple to use, manufacture and construct and can be made from a variety of inexpensive materials. The advantages of the invention are basically attained by producing an apparatus comprising a body having a length and a width suitably dimensioned to be held in the hand of an operator and to support a length of IV tubing. The body further includes at least one holding means for removably attaching the tubing to the body without restricting the flow of fluids through the tubing.

In preferred embodiments of the invention the body further includes a pair of flanges extending outwardly from each end of the body. The body member preferably has an elliptical shape having a major axis and a minor axis. The flanges are preferably shaped to complement the shape of the body to form a spool-like assembly. The elliptically shaped body is generally preferred to provide an elongated surface with a modest curvature to support the coupling in a manner to be easily accessed and punctured by the hypodermic needle. The elliptical shape also supports the IV tube and coupling so that in the event of the needle slipping or breaking, the operator's hand is protected from injury.

The holding means for securing the tubing in place on the body may be a slot or groove in the outer edge of the flange. The notch is generally dimensioned so that the tubing fits snugly in the slot without pinching or excessive bending of the tubing which would otherwise restrict the flow of fluids through the tubing.

In further embodiments of the invention the apparatus includes means for coupling the body to a similar body to form a multi-ganged assembly. At least one of the flanges is removably coupled to the body by a mounting pin extending axially from the body. The mounting pin is generally shaped with a notch to provide alignment of the flange on the body. The opposite end of the body includes a recess to receive the axial pin of an adjacent body.

These and other salient advantages and features of the invention will become apparent from the following detailed description of the invention and the drawings.

BRIEF DESCRIPTION OF THE DRAWINGS

In order to impart full understanding of the manner in which these and other objects are attained in accordance with the invention, a particularly advantageous embodiment thereof will be described with reference to the accompanying drawings, which form a part of this disclosure, and wherein:

FIG. 4 is a perspective view of the embodiment as seen from the right side of FIG. 3 illustrating the coupling recess;

FIG. 5 is a side view of the assembly as taken from the right side of FIG. 3;

FIG. 6 is an exploded view of the embodiment of FIG. 3;

DETAILED DESCRIPTION OF PREFERRED EMBODIMENTS

The disadvantages and limitations of the previous holding devices and storage devices for intravenous tubes and the like are obviated by the present invention while providing a convenient and safe assembly for handling IV tubes. The present invention is primarily directed to an assembly for securing an IV tube and supporting a coupling in a fixed and safe position while an operator inserts a hypodermic needle into the coupling.

The assembly of the invention is generally for use with conventional IV tubing and couplings as known in the art and as typically used in the medical field. The typical IV tubing is a thin wall, flexible tubing having an outer diameter of about 3–5 mm although other sizes of tubing may be used.

Figure 1:
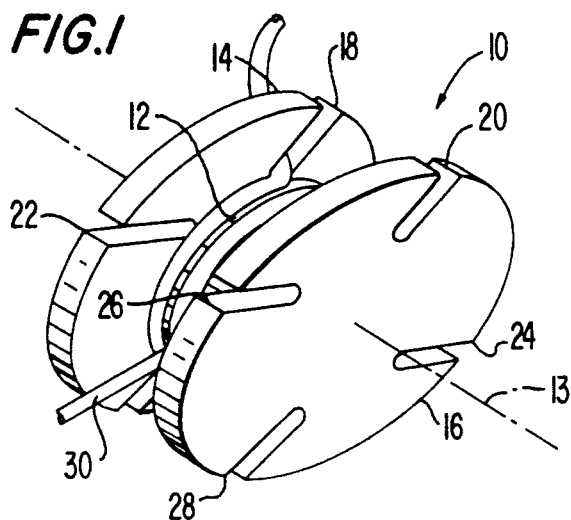
FIG. 1 is a perspective view of the apparatus in accordance with a first embodiment of the invention.
Figure 2:
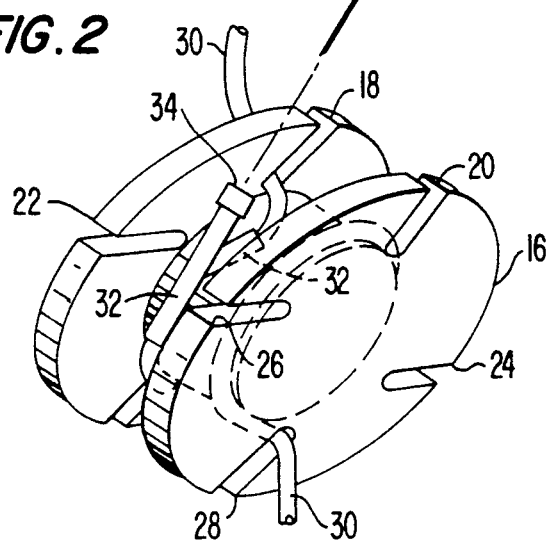
FIG. 2 is a perspective view of the apparatus having an IV tube partially wound on the apparatus with the coupling exposed.

Referring to FIGS. 1 and 2, the invention in a first preferred embodiment comprises a holding and storage assembly indicated generally at 10 including main body section 12. The body 12 is depicted in FIG. 1 as having an outer surface with an essentially elliptical cross section. The elliptical cross section has a major axis and a minor axis in a ratio of about 1.3:1. Body 12 is dimensioned to be easily held in the palm of the hand and has sufficient length, about 75 to 125 mm along the major axis, to simultaneously support a section of tubing and a coupling member without crimping the tubing or otherwise restricting the flow of fluids.

In the embodiment of FIG. 1, a pair of flanges 14 and 16 extend radially outwardly from each end of the body 12. As shown, the flanges 14, 16 each have an elliptical shape corresponding substantially to the cross sectional shape of the body 12, but larger. Flanges 14, 16 preferably extend from the body 12 a sufficient distance to allow several windings of tubing around the body, e.g., 12 to 25 mm, thereby providing storage of three or four layers of excess length of tubing. This radial height of the flanges should not, however, be so high as to interfere with the handling of the tubing.

A plurality of holding means are included on each flange to removably couple the tubing to the assembly 10 during use. As shown in FIG. 1, the holding means are preferably slots 18, 20, 22, 24, 26 and 28 extending inwardly toward main body 12 from the peripheral edge of each of the flanges. The walls of the slots can be formed axially with respect to the central axis of the flanges and the body, i.e., perpendicular to the end surfaces of the flanges. In preferred embodiments, each slot is formed at an angle with respect to the central axis of the flanges and the axis of the body and extends inwardly to a point contiguous with body 12. Stated differently, each slot can be thought of as having side walls lying in generally parallel planes which do not include the central axis of the ellipse containing the outer surface of main body 12. Generally, the slots are at about 45° to center axis 13 so that the tube can be snapped into the slot and wound on the body without crimping the tube, thereby to avoid restricting the flow through the tube. The widths of the slots are chosen to complement the dimensions of the flexible tubing to ensure a friction fit to secure the tubing in place during use without collapsing the tube. The width of a slot in a preferred embodiment is about 2–4 mm to accommodate a conventional IV tube. The width may be larger or smaller to accommodate different sizes of tubing.

Figure 8:
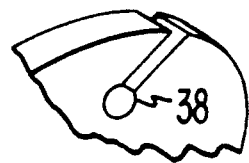
FIG. 8 is a partial view of the tube holding means in a further embodiment.

The slots may be formed to have a uniform width throughout the length to define a U-shaped slot terminating at a rounded bottom as shown in FIG. 1. In alternative preferred embodiments as shown in FIG. 8, the slots are formed to have an enlarged circular area 38 at the bottom of the slot to conform to the outer dimension of the tubing and to define a more restricted inlet portion to prevent tube from sliding out of the slot without applying an intentional outward force. In this manner, the slot provides more of a snap fit to securely hold the tubing in place without crimping the tubing while fluid is flowing therethrough. When formed with circular area 38, the walls of a slot can be canted relative to axis 13 to further minimize the possibility of sharp bends in the tubing.

The slots are further formed to extend inwardly toward the body a sufficient distance to effectively grip the tubing and to position the tube on the body so as to support the tubes and the coupling. Preferably, the slots extend close to the outer surface of the body.

The actual number and position of the slots is not critical so long as a sufficient number of slots are provided on each flange to effectively retain the tubing and the coupling on each flange and body assembly without crimping the tube and to provide a selection of locking locations for tubing, depending on where the wound tubing is best allowed to leave the main body. In one embodiment, slots 18 and 22 may be formed at each end of the assembly along the major axis of the elliptical shaped body. Generally at least two slots are provided on each side of the flange as illustrated in FIG. 1.

In preferred embodiments, each flange has at least two slots as shown in FIG. 1. Additional slots may be included as desired. Generally each flange will have a pair of slots 20 and 26 on one arcuate section of the peripheral edge positioned at a first angle with respect to the axis of the body and a second pair of cooperating slots 24, 28 on the opposite arcuate section of the peripheral edge and disposed at an equal and opposite angle. In the embodiment of FIG. 1, the slots 20, 26 are disposed along the major axis of the elliptical flange 16 at opposite ends. The slots are angled with respect to the body such that each slot on the flange 14 is substantially parallel with an opposing slot on the second flange. The slots are preferably arranged so that a section of tubing can be secured in a slot on first flange 14 and extend to a second slot in second flange 16 with the coupling device disposed between the flanges and without the tubing being crimped.

In operation and use of assembly 10 as depicted in FIG. 2, IV supply tubing 30 is snapped into a first slot 18 of flange 14 and held in place by a friction fit. The tubing 22 is positioned on the assembly 10 so that coupling 32 is positioned generally parallel with the major axis of body 12 to act as an injection port. Coupling 32 as illustrated is typically a y-shaped member having two legs coupled to tubing 30 and a third leg terminating at a distal end with a puncturable septum 34. Coupling 32 is positioned on body 12 such that puncturable septum 34 is directed away from the body as shown in FIG. 2. Tubing 30 may be placed on the assembly 10 to extend directly from slot 18 on first flange 14 to slot 26 on second flange 16. Alternatively, tubing 30 may be wrapped around body 12 one or more turns and then snapped into slots 18 and 26 on the flanges. In this fashion, assembly 10 is able to provide storage of the tubing 30 while the tubing is not in use and to provide storage of excess lengths of tubing while supporting coupling 32.

The elliptical shape of body 12 is particularly desirable so that the major axis of the ellipse provides a substantially non-planar elongated surface with some curvature. By positioning coupling 32 along the major axis of the ellipse, the puncturable septum 34 faces outwardly from the assembly for easy access by the operator. In use, the operator grasps assembly 10 in the palm of the hand with the thumb and fingers grasping the outer faces of flanges 14 and 16. The operator is then able to insert a hypodermic needle 36 through septum 34 with ease and safety. Assembly 10 holds the coupling in a position such that the hypodermic needle is pointed away from the operator's hand during insertion of the needle into septum 34. Body 12 and flanges 14, 16 effectively shield the hand from accidental puncture in the event the needle should slip or break. Tubing 30 and coupling 32 can then be removed from the assembly by pulling the tubing from the slots without damaging the tubing or coupling.

Assembly 10 is preferably formed from a lightweight plastic material using conventional molding processes. The assembly may be formed from a solid block of material, although hollow injection molded structures are preferred to reduce material costs and weight. The material from which the assembly is formed should be sufficiently strong to prevent accidental penetration by a hypodermic needle.

In an alternative preferred embodiment of the invention depicted in FIGS. 3-6, an assembly 40 comprises a first flange 42 fixedly attached to a body 44 and a second flange 46 removably coupled to the opposite end of the body 44. As in the embodiment of FIG. 1, body 44 preferably has an elliptical cross section with a major axis and a minor axis. Typically, the body has a minor axis of about 35 mm, a major axis of about 55 and an axial length of about 15 to 25 mm.

First flange 42 and second flange 46 preferably have elliptical shapes corresponding to the shape of body 42. Flange 42 may be integrally formed with the body at the time of manufacture or assembled in a later manufacturing step.

Second flange 46 is removably coupled to body 44 so that the flange can be removed as discussed hereinafter in greater detail. Body 44, as best illustrated in FIG. 6, includes a non-circular stem 48 extending axially from one end of the body. In preferred embodiments, stem 48 includes at least one flat face 50. Second flange 46 includes a central aperture 52 shaped and dimensioned to correspond to stem 48 to define a mating socket. As shown, socket 52 passes entirely through the separable flange and also includes a flat face 54 such that the flange 46 is mounted non-rotatably on stem 48. In addition, flat face 50 on stem 48 and flat face 54 of sockets 52 provide proper orientation of second flange 46 with respect to body 44 and first flange 42. Preferably, second flange 46 is the same size and shape as the first flange and coupled to body 44 to form a symmetrical assembly. Socket 52 is dimensioned to provide a fiction fit on stem 48 which is sufficiently tight to hold the assembly together during use without additional fastening means.

In a further embodiment shown in FIG. 6, a detent 56 is provided on flat face 50 of stem 48 to retain flange 46 in place. Socket 52 may also include a complementary recess 58 on flat face 54 to provide a snap-type interference fit with stem 48. Stem 48 and socket 52 also may be tapered to facilitate correct assembly of the flange on the stem.

In the embodiments shown in FIGS. 3-7, stem 48 includes flat face 50 to selectively orient flange 46 on the stem with respect to the body. In alternative embodiments, the stem may be splined or may include a key to orient the flange on the stem.

Referring to FIG. 4, first flange 42 also includes a recess to define a socket 70 matching the shape of stem 48. As shown, socket 70 includes a flat face 72 to cooperate with flat face 50 of stem 48. As discussed hereinafter in greater detail, socket 70 provides a means to removably couple the assembly 40 to a similar assembly.

Figure 3:
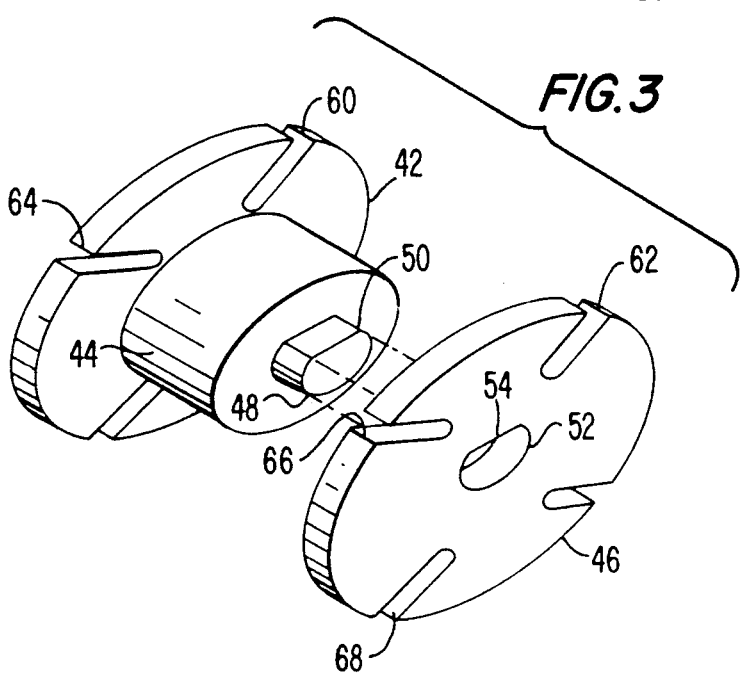
FIG. 3 is a perspective view of a further embodiment of the invention illustrating the removable flange.

Flange 42 also include slots 60 and 64, extending inwardly from its peripheral edge. Slots 60 and 64 are preferably angled with respect to the axis of body 44. As shown in FIG. 3, flange 42 includes first slot 60 and second slot 64 disposed at opposite ends of the major axis and angled in the same direction. Second flange 46 includes slots 62 and 66 disposed in the peripheral edge and angled substantially parallel to slots 60 and 64.

Figure 7:
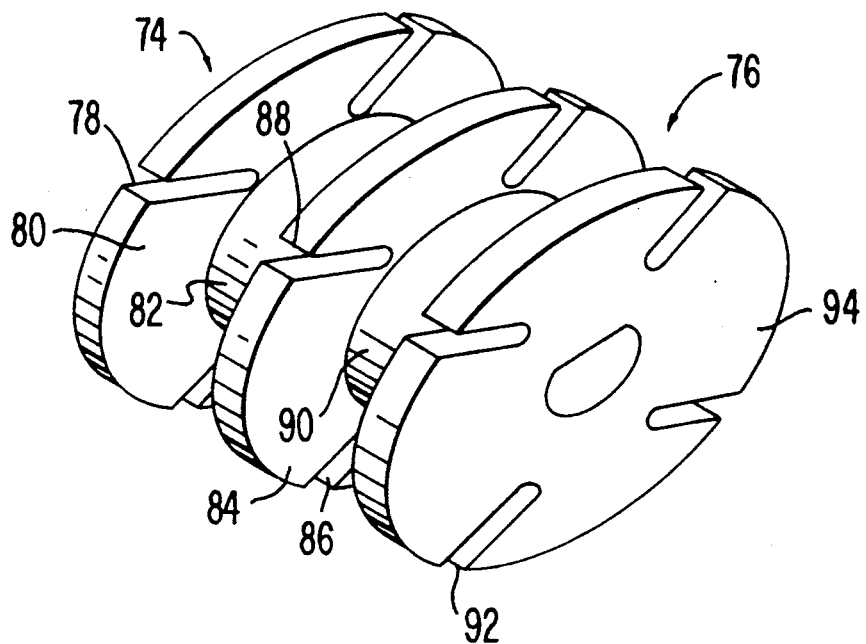
FIG. 7 is a perspective view of the apparatus of the embodiment of FIG. 3 assembled in a ganged manner.

The assembly in the embodiment of FIGS. 3-6 may be used in the manner of the embodiment of FIG. 1 or assembled in a ganged fashion as shown in FIG. 7. To join several of the assemblies 40 together, socket 70 is provided in the outer face of first flange 42. Socket 70 corresponds to and is dimensioned to receive a stem 48 of an adjacent assembly. In operation, the second flange 46 of a first assembly 74 is removed from its stem 48 and the stem is inserted into a socket 70 in a second assembly 76. Although only two such assemblies are shown joined in FIG. 7, any number of assemblies may be coupled together. The resulting combination of several assemblies as shown in FIG. 7 is used in a manner similar to the embodiment of FIG. 1 to support a plurality of IV supply tubings and couplings delivering, for example, a plurality of different medications or support fluids to the patient. In a preferred form of the invention, a first IV tube is snapped into slot 78 of a first flange 80 of the assembly 74 and extended across the body 82 to a flange 84 of the second assembly 76 and snapped into slot 86. A second IV tube can then be snapped into a slot 88 on the flange 84 and extended across body 90 of assembly 76 and snapped into a slot 92 on flange 94.

Although preferred embodiments of the invention have been described herein, it is to be understood that numerous alternative embodiments can be envisioned by one skilled in the art without departing from the spirit and scope of the invention as defined in the appended claims.

What is claimed is:

1. A device for supporting an intravenous tube comprising the combination of
   a body having a predetermined length and width selectable to be holdable in a human hand, said body having an outer surface with a substantially elliptical shape; and
   holding means for removably fixing an intravenous tube to said body substantially without restricting flow of fluids through said tube.

2. The device according to claim 1, wherein said body has a central portion with opposite ends, said body further comprising first and second flanges extending radially outwardly from said opposite ends of said central portion.

3. The device according to claim 2 wherein said holding means is disposed in a peripheral edge of at least one of said flanges.

4. The device according to claim 3 wherein said holding means comprises a first slot in said first flange.

5. The device according to claim 4, said holding means further comprising a second slot in said second flange.

6. The device according to claim 5 wherein said first and second slots are formed in said flanges diagonally with respect to a central axis of said flanges.

7. The device according to claim 5 wherein said second slot is spaced from said first slot in an arcuate direction with respect to a central axis of said body.

8. The device according to claim 5 wherein said first and second slots have a substantial U-shaped cross-section.

9. The device according to claim 5 wherein said first and second slots have a restricted portion at an upper end adjacent a surface of said flanges.

10. The device according to claim 2 wherein at least one of said first and second flanges is removably attached to said body.

11. The device according to claim 10 wherein said body has means for removably coupling to a second body for supporting a second intravenous tube.

12. A device for supporting an intravenous tube comprising the combination of
   a body having a central portion with opposite ends, a substantially elliptical cross-section with a major axis and a minor axis and first and second flanges extending radially outwardly from said opposite ends of said central portion, said first and second flanges being substantially elliptically shaped to correspond to the shape of said body; and
   holding means comprising a first slot disposed in a peripheral edge of said first flange and a second slot in said second flange for removably fixing an intravenous tube to said body substantially without restricting flow of fluids through said tube.

13. The device according to claim 12 wherein said first slot is disposed substantially at a first end of said first flange along said major axis and said second slot is disposed at an opposite end of second flange along said major axis.

14. An assembly for supporting a length of an intravenous tube including puncturable coupling means for introducing a material to said tube by syringe, said assembly comprising
   a body having a non-planar continuous surface for supporting an IV tube with said tube wound around said body, said body having first and second axial ends;
   a first flange coupled to said first axial end of said body, said first flange having a shape corresponding to a cross-sectional shape of said body;
   at least one first tube coupling means on a peripheral edge of said first flange; and
   a second flange removably coupled to said second axial end and having at least one second tube coupling means on a peripheral edge of said flange whereby said tube can be removably coupled to said first and second flanges to support said tube and puncturable coupling means on said body.

15. The assembly of claim 14 further comprising means for coupling to at least one second assembly.

16. The assembly of claim 14, said stem further including at least one detent extending radially outward and said aperture in said second flange includes at least one complementary recess on an inner surface of said flange.

17. The assembly of claim 14 further comprising means for removably coupling said second flange to said body, said means comprising a stem extending substantially axially from said second axial end of said body and said second flange including an aperture axially disposed in said second flange defining an inner socket and being dimensioned to complement said stem.

18. The assembly of claim 17, said stem and second flange including means to selectively orient said second flange on said stem and prevent rotation of said second flange on said stem.

19. The assembly of claim 18 wherein said means to prevent rotation of said second flange on said stem comprises a substantially flat outer face on said stem and a substantially flat face on an inner socket of said second flange.

20. The assembly of claim 18 for supporting a plurality of intravenous tubes, each tube including a puncturable septum means for introducing a fluid to said tube by a syringe and hypodermic needle assembly, said assembly comprising:
   a first body dimensioned to be capable of having a tube wound around said body, said body having first and second axial ends;
   a first flange coupled to said first axial end of said body, said first flange having an outwardly facing axial recess defining a first socket, said first flange further having at least one slot in a peripheral edge to removably receive said tube on a friction fit relationship;

a first axial stem extending outwardly from said second end of said body;

a second body removably coupled to said axial stem; said second body corresponding to said first body and having a first axial end and a second axial end, a first flange coupled to said first axial end and at least one slot in a peripheral edge of said flange, a socket axially disposed in said first end corresponding to said first axial stem, and a second flange coupled to said second axial end and having at least one slot formed in a peripheral edge of said second flange.

* * * * *